United States Patent [19]

Denis et al.

[11] 4,168,430

[45] Sep. 18, 1979

[54] PROCESS AND APPARATUS FOR MONITORING THE QUALITY OF WELD SPOTS PRODUCED BY RESISTANCE SPOT WELDING

[75] Inventors: Jean F. Denis, Lesigny; Serge I. Dzalba-Lyndis, Guyancourt; Robert L. Kuchelbecker, Chatillon sous Bagneux; Jean A. V. Petit, Saint Cloud, all of France

[73] Assignee: Societe Nationale Industrielle Aerospatiale, Paris, France

[21] Appl. No.: 850,061

[22] Filed: Nov. 9, 1977

[30] Foreign Application Priority Data

Nov. 17, 1976 [FR] France .............................. 76 34574

[51] Int. Cl.² .............................................. G01J 1/00
[52] U.S. Cl. ..................................... 250/338; 250/342
[58] Field of Search ............... 250/330, 333, 338, 340, 250/342; 358/113

[56] References Cited

U.S. PATENT DOCUMENTS

| | | | |
|---|---|---|---|
| 3,191,441 | 6/1965 | Erickson | 250/338 X |
| 3,245,509 | 4/1966 | Larson | 250/338 X |
| 3,868,508 | 2/1975 | Lloyd | 250/338 X |
| 3,924,130 | 12/1975 | Cohen et al. | 250/342 |
| 4,023,201 | 5/1977 | Faulkner | 250/342 X |

Primary Examiner—Davis L. Willis
Attorney, Agent, or Firm—Merriam, Marshall & Bicknell

[57] ABSTRACT

The invention relates to a method and apparatus for monitoring the quality of weld spots produced by resistance spot welding according to which a weld spot which has just been made is observed by means of a video camera sensitive to infrared radiation at a well determined instant of its cooling, with a view to comparing it with a reference weld spot observed previously under the same conditions; the value and passage of the welding current is controlled by means of the video signal and the synchronization signals coming from said camera, which signals are exploited to make an image reconnaissance by counting scanning lines or dots defined along the lines by a clock, when this video signal becomes greater than an electrical voltage representative of the level of emission of infrared radiation of the periphery of the reference weld spot.

13 Claims, 8 Drawing Figures

PROCESS AND APPARATUS FOR MONITORING THE QUALITY OF WELD SPOTS PRODUCED BY RESISTANCE SPOT WELDING

The present invention relates to a process and apparatus for monitoring the quality of weld spots produced by resistance spot welding.

It is known that, when elements to be assembled together are spot-welded, numerous defects may occur which are detrimental to the solidity of the assembly. Such defects may consist in the appearance of cracks, pinholes, porosity or malformations of the spots and may have various causes, such as:

- failure of the welding apparatus either in the regulation of the welding current or in the count of the time during which the welding energy is released, or in the application of the pressure between the electrodes, which may be in the form of a plate, wire, roller, etc.
- physicochemical surface state of the elements to be assembled together;
- state, form, hardness of the electrodes;
- quality of the electrical contacts in the welding circuit;
- defective insulations producing losses of current; etc.

Monitoring of the resistance spot weldings is usually generally of the destructive type, i.e., they consist in macroscopic or macrographic examinations, shearing tests (traction and torsion), tearing tests (tearing apart of the assembled pieces), etc. These examinations are all made either on test pieces representative of the assembly to be made or by taking a few finished pieces from a large batch. Consequently, this monitoring cannot guarantee all the welds made.

Radiographic monitoring is not destructive but it is delicate to carry out and interpret. It allows most of the internal defects of the weld spots to be revealed, but an assessment of the dimensions of the melts (i.e., the masses of molten metal of the weld spots) is generally not possible and even less so is an assessment of the penetration of said melts in the elements to be assembled. Furthermore, this type of monitoring is possible only a posteriori. Consequently, the possible defects may affect numerous welded assemblies before they are detected.

To remedy the drawbacks of the above-mentioned methods of monitoring, it has already been proposed to observe the weld spots which are still hot by means of an infrared video camera. Thus, said camera may furnish on the screen of a cathode-ray tube a temperature chart of the weld spot, each isothermal zone of the chart corresponding to a colour or a specific intensity. This chart is then used for monitoring the quality of the weld spot which it represents. To this end, said chart is compared with a reference chart, representing the spectrum of a weld spot considered as model. The comparison is made visually by juxtaposition of the reference chart with the chart on the screen. Such a method therefore requires a great deal of time and cannot give a fine analysis. The rate of monitoring the weld spots is slow and causes considerable eye strain for the observer. A method of this type is therefore not suitable for continuously monitoring the weld spots of an assembly which requires a plurality of closely spaced weld spots.

Furthermore, French patent application No. 73 33705 discloses a device enabling the overall energy radiated in an infrared frequency band by a weld spot to be measured, enabling a signal proportional to this energy to be produced and said signal to be compared with a reference signal.

Such a device allows a rapid monitoring but with low precision. In fact, this device allows only a rough assessment of the dimensions of the monitored weld spots and cannot suffice for monitoring assemblies having to satisfy strict criteria of quality, such as vital elements used in aerospace.

The present invention obviates these drawbacks of the known methods and allows a rapid, precise and automatic monitoring of the weld spots produced by resistance spot welding. In addition, it allows the regulation of the welding current to compensate the variations in supply, contact resistance of the connections of the power loop, and magnetic intensity of said loop.

To this end, according to the invention, the method for monitoring weld spots produced by resistance spot welding, according to which a weld spot which has just been made is observed by means of a video camera sensitive to infrared rays, at a determined instant of its cooling, with a view to comparing it with a reference weld spot observed previously under the same conditions, is noteworthy in that the value and passage of the welding current is controlled by means of the video signal and the synchronisation signals coming from said camera, which signals are exploited to make an image reconnaissance by counting scanning lines or dots defined along the lines by a clock, when this video signal becomes greater than an electrical voltage representative of the level of emission of infrared radiation of the periphery of the reference weld spot.

In this way, it is possible to monitor the weld spots formed by a high performance welding apparatus at a high rate and with high precision.

According to a further feature of the invention, with a view to comparing the length of the weld spot under observation with that of the reference weld spot, the numbers of scanning lines of the camera corresponding to said weld spots under observation and to said reference weld spot are measured and compared. Moreover, it is advantageous to count and compare, scanning line by scanning line, numbers of imaginary dots determined by dividing said scanning lines, so as to allow the comparison of the width of the weld spot under observation with that of the reference weld spot.

Preferably, in addition to the comparisons of length and width, in order to increase the precision of the control, the totality of the imaginary dots corresponding to the totality of the scanning lines are counted, this giving a representation of the surface of the weld spot which may be compared with a corresponding representation of the reference weld spot.

The control of the welding current preferably depends on said surface comparison.

Finally, it is also advantageous to judge the axial dissymmetry of the weld spot under observation and, to this end, the theoretical longitudinal axis of this weld spot is determined from the reference weld spot and, scanning line by scanning line, imaginary dots determined by dividing said lines are observed, said imaginary dots being counted up to the longitudinal axis and counted down therefrom.

In this way, by comparing the lengths, widths, surfaces and axial dissymmetry, a high-precision control may be obtained.

To carry out the method according to the invention, a welding apparatus comprising a mobile welding head advancing step by step or continuously, is noteworthy in that it comprises, on the one hand, a video camera sensitive to infrared radiation, securely fastened to said welding head and directed towards a weld spot which has just been made and, on the other hand, an electronic arrangement receiving the video signal and the synchronisation signals from said camera and transmitting to said head or to its annexes signals enabling the welding current to be regulated and the functioning of said apparatus to be controlled.

To allow an auxiliary monitoring of the quality of the weld spots, it is possible to associate with the apparatus a cathode-ray tube receiving the video signal and the synchronisation signals from the camera and to provide a translucent plate on which is reproduced the image of the infrared radiation of the reference weld spot, the temperature zones of said image reproduced on said translucent plate being coloured with complementary colours corresponding to the colours with which the infrared image of the weld spot under observation is reproduced on the screen of the cathode-ray tube, the image of said weld spot under observation being observed through said translucent plate. In this way, when the two infrared images of the reference weld spot and of the weld spot under observation are in perfect coincidence (which corresponds to the good quality of the weld spot), under observation only uniformly black or brown shading is visible to the observer, whereas, when the quality of the weld spot under observation differs from that of the reference weld spot, different coloured zones appear to the observer.

The method and device according to the invention are applied particularly but not exclusively to the quality control of the assembled structures of the sandwich type, the lightness and rigidity of which render them much appreciated in the construction of aircraft.

Such structures comprise a thick and not very dense core inserted between two sheets, the whole being assembled by gluing, welding or brazing.

Glued assemblies are suitable for structures used in normal ambient conditions and are not suitable when said structures must be used at high temperature.

Brazed assemblies are suitable for structures used at high temperature, but they are expensive to produce and require that all the masses to be assembled together be brought to brazing temperature, this possibly altering certain mechanical qualities of the materials used. This is why assemblies made by resistance spot welding are preferred.

The non-destructive monitoring of the glued or brazed assemblies does not presently raise any particular problems and different techniques are known and efficient. In these cases, in view of the high relative value of the surfaces assembled and connected together, it is possible to allow the existence of poorly assembled zones. This is no longer possible in the case of assembling by resistance spot welding, all the more so as such a weld, when it is defective, is rarely isolated.

The non-destructive monitoring of the assemblies made by resistance spot welding raises a problem which, up to the present time, has not found an entirely satisfactory solution. This gap is particularly felt in the aerospace industry which, for obvious reasons of safety, requires formal guarantee as to the quality of the assemblies effected.

The structures, particularly of the sandwhich type, and more especially those with an undulating core, are most often assembled by resistance spot welding. These weld spots are generally made with a roller, successively and at a high rate. Monitoring must be simultaneous, therefore rapid, and must allow the immediate stopping of the operations when a defective weld is detected.

The invention will be more readily understood on reading the following description with reference to the accompanying drawings, in which.

Figure 1:
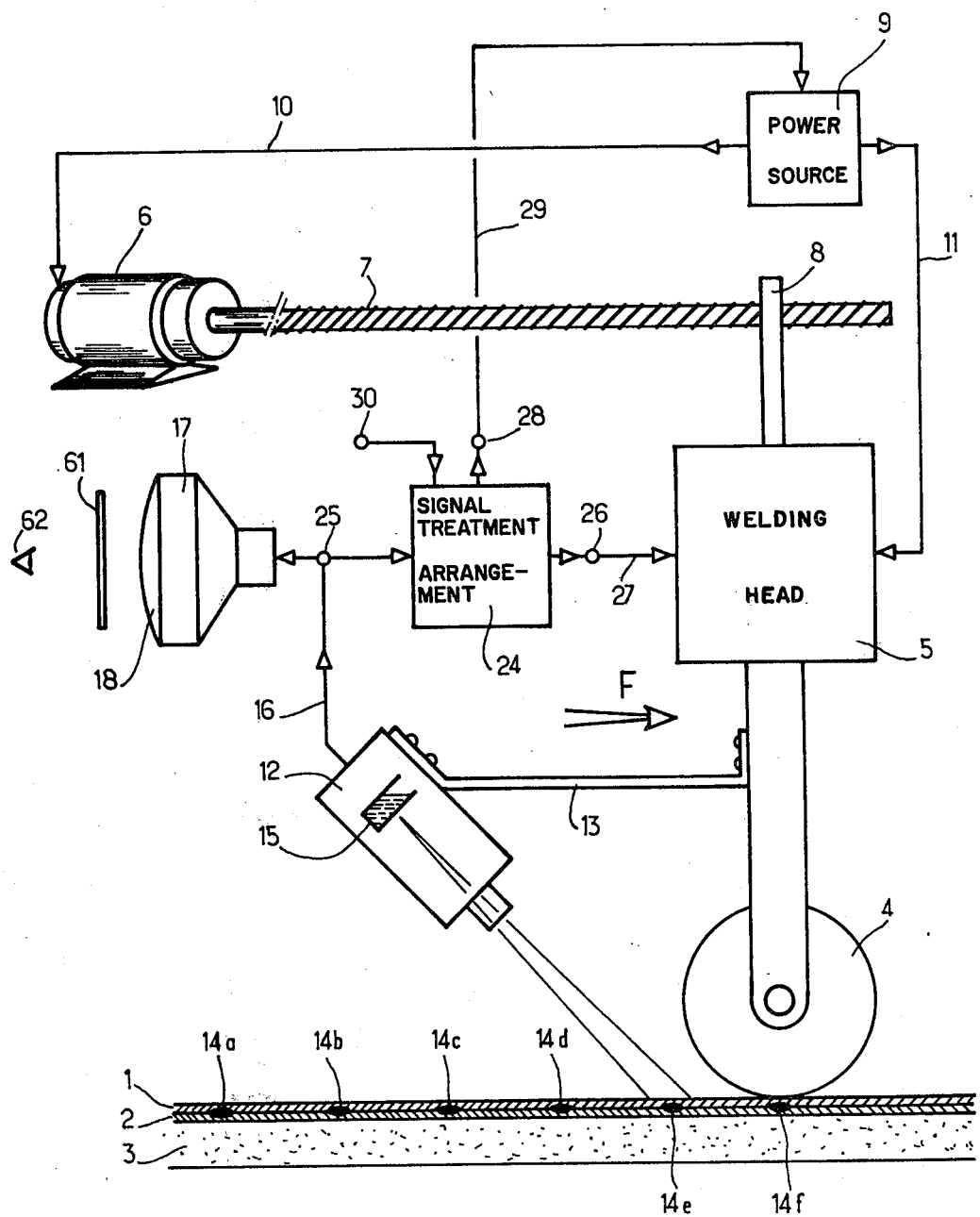
FIG. 1 is a schematic view of an embodiment of the device according to the invention.

Referring now to the drawings, FIG. 1 schematically shows the device according to the invention which is in the process of assembling two pieces 1 and 2 together by resistance spot welding.

These pieces are disposed on a metal plate 3 and a welding roller 4 presses said pieces against said plate. The roller 4, shown very schematically in the drawing, is mounted to rotate freely on a welding head 5 which moves in the direction of arrow F under the action of a step by step or continuously rotating electric motor 6 driving an endless screw 7, cooperating with a nut 8 fast with the welding head 5. The motor 6 and the welding 5 are fed by a source of current 9, via lines 10 and 11 respectively.

A special video camera 12, sensitive to the radiations of the infrared band, is fixed to the welding head by means of a rigid arm 13. Such a welding arrangement enables weld spots 14a to 14f to be made between pieces 1 and 2, spots 14a to 14e having already been effected, whilst spot 14f is in the process of being made. The camera 12 is directed towards weld spot 14e, which has just been made, so as to be able to observe said spot at a precise instant of its cooling. In this way, at this well determined instant, the camera 12 picks up the infrared radiation of the weld spot 14e in the process of cooling. This radiation is focussed on a detector 15, sensitive to the spectrum of the infrared radiation band. The detector 15 may for example be of the type with indium antimonide stabilised with liquid nitrogen and may present a maximum sensitivity for those radiations whose wave lengths are included between 1 and 6 micrometers.

Of course, the camera 12 each time observes that cooling weld spot which precedes according to the direction of displacement of the welding head, the weld spot which is being produced. In this way, at the output 16 of the camera 12, video signals are obtained which are representative of the temperature chart of the weld point under observation, at the instant of observation in question.

If a cathode-ray tube 17 is connected to the output 16 of the camera 12, these video signals which are possibly amplified and processed, furnish on the screen 18 of this tube an enlarged image of the temperature chart of the spot under observation, so that a colour or specific coloured intensity corresponds to each isothermal zone or line, it being understood that the cathode-ray tube 17 may be of the black and white or colour type.

Figure 2:
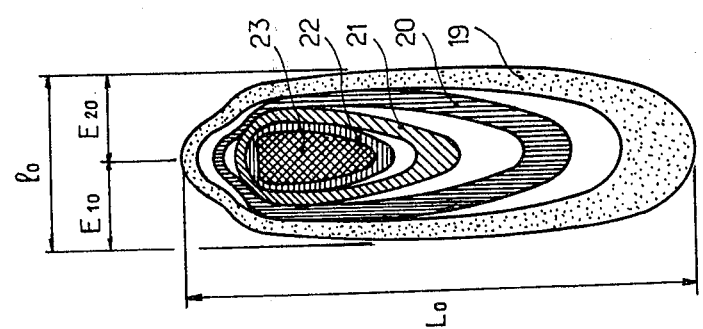

FIGS. 2 to 5 show examples of temperature charts for different weld spots, as may appear on screen 18. FIG. 2 shows the infrared image of a weld spot which is considered as being correct. The isothermal zones 19, 20, 21, 22 and 23 are shown to be clearly defined and the contour and size of the image reproduce the shape of the welded zone and its relative dimensions. Of course, the temperatures of the zones decrease from the innermost zone 23 to the outermost zone 19.

Figure 4:
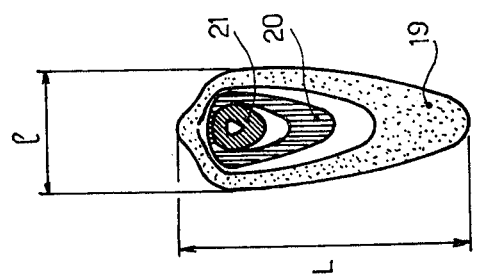
Figure 3:
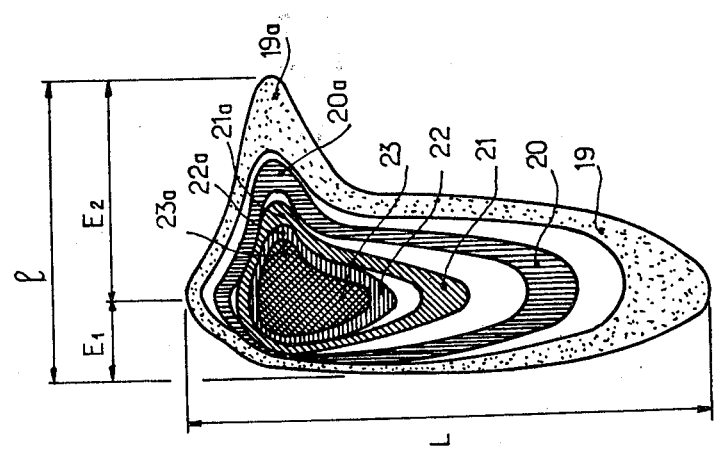

FIG. 3 shows the infrared chart of a so-called "expelled" weld spot, i.e., having an axial dissymmetry, the isothermal zones 19 to 23 having lateral protuberances 19a to 23a. Such a defect is due to the fact that the electrical welding energy was excessive; the weld spot has become very large and has given rise to a lateral expulsion of the molten metal. In this case, the modifications of the isothermal zones with respect to the correct weld spot of FIG. 2 are obvious. FIG. 4 illustrates a weak weld spot whose infrared spectrum does not comprise the hottest zones 22 and 23, whilst FIG. 5 shows the chart of the isothermal zones of an insufficient weld spot, i.e., its melt presents a slight penetration in at least one of the pieces 1 and 2 to be assembled together.

Figure 5:
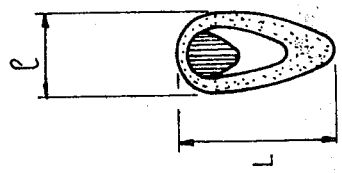
FIGS. 2 to 5 show the infrared images of various types of weld spots.

In the case of FIGS. 4 and 5, the isothermal image is clearly smaller than that of the correct weld spot of FIG. 2, whilst moreover the shape thereof is different. The basic principle of the invention is to measure, for a weld spot under observation, its length L, its width l and to compare them with the corresponding dimensions Lo and lo of a correct weld spot, as well as to determine whether the weld spot is symmetrical with respect to its longitudinal axis by comparing, with respect thereto, its half-widths $E_1$ and $E_2$. Of course, in the case of a correct weld spot, the left half-width $E_{10}$ is substantially equal to the right half-width $E_{20}$. Furthermore, these verifications may be completed by comparison of the total surface So of the reference spot.

To this end, the device according to the invention comprises an electronic arrangement 24 whose input 25 receives the video signal and the synchronisation signals coming from the output 16 of the infrared camera 12 and corresponding to a precise instant of cooling of a weld spot (counted for example from the electrical welding pulse having provoked the formation of the corresponding melt), said arrangement 24 exploiting these video signals to verify the length, width, surface and symmetry of the weld spot under observation to compare them automatically with the same dimensions of a reference weld spot.

The exploitation of the video signals from camera 12 by the electronic arrangement 24 is such, according to the invention, that it may, on the one hand, regulate the welding current and, on the other hand, stop the welding apparatus when the welds become defective, i.e., when one of the sizes L, l, $E_1$, $E_2$ or S is no longer within the predetermined limits. To this end, the arrangement 24 comprises an output 26 which, via a line 27, controls the regulation of the welding current of the head 5 and an output 28 which, via a line 29, may stop the operation of the welding apparatus.

According to the invention, the video signal and the synchronisation signals issuing from the camera 12 are exploited to effect an image reconnaissance by counting the scanning lines or dots defined along the lines by a clock, when the video signal exceeds a level determined by a comparator.

Figure 6:
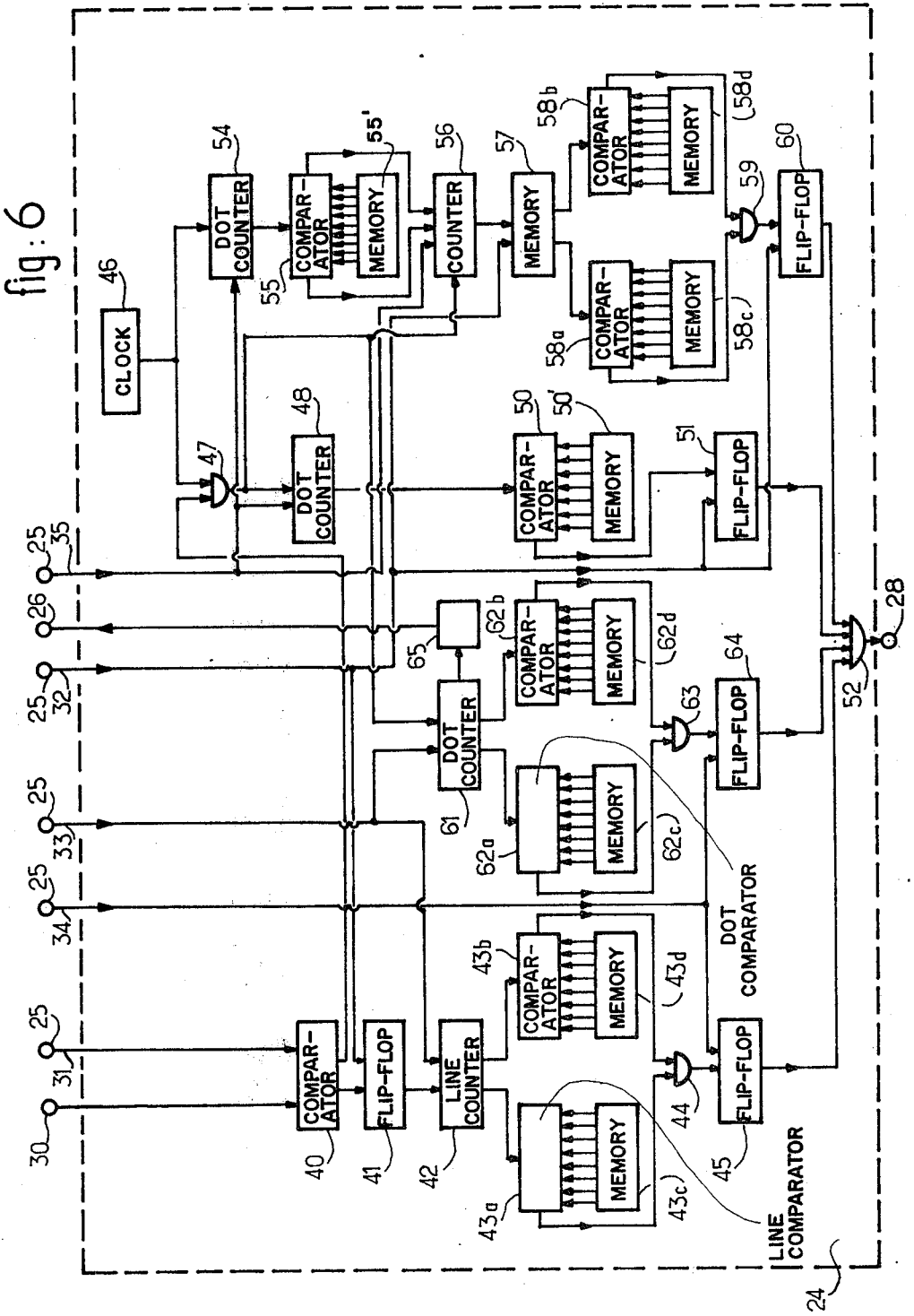
FIG. 6 shows the block diagram of the device according to the invention.

FIG. 6 illustrates an embodiment of the arrangement 24 of FIG. 1.

This embodiment comprises an analog comparator 40 which delivers a signal when the video signal coming from camera 12 via a lead 31 exceeds the level determined by a reference voltage which corresponds to the desired level of infrared emission of the edge of the melt and applied on a terminal 30. Said comparison signal validates a flip flop 41 and an AND gate 47 which also receives the signals from a clock 46. Said flip flop 41 is reset to zero by signals indicating end of scanning line of camera 12 coming from terminal 25 via a lead 32 and therefore furnishes a signal at each line, when the video signal exceeds the reference voltage. The signals furnished by the flip flop 41 are counted by a line counter 42 reset to zero by the beginning of image signal coming from the terminal 25 via lead 33, and the counting is compared with a maximum number of lines in a comparator 43a and with a minimum number of lines in a counter 43b, for each scanned image. To this end, the comparator 43a receives from a memory 43c the maximum number of lines which corresponds to a maximum length of weld spot not to be exceeded, whilst it receives from a memory 43d the minimum number of lines which corresponds to a minimum length of weld spot not to be exceeded. The outputs of the comparators 43a and 43b are connected by means of an OR gate 44 to a flip flop 45 which is reset to zero by the end of image signal issuing from said camera and coming from terminal 25 via a lead 34. If the comparator 43a sees too high a number of lines, or if the comparator 43b sees too low a number of lines, they deliver a signal to the flip flop 45 which delivers a signal to an OR gate 52, the output of which is connected to terminal 28 to enable the welding apparatus to stop via line 29.

Similarly, assembly 61, 62a, 62b, 62c, 62d, 63 and 64 determines the possible defects in surface area of each weld spot. The counter 61 of dots validated per image receives a signal from the AND gate 47, when the video signal corresponds to the surface of the weld spot monitored. Said signal coming from the AND gate 47 constitutes in fact a determined number of dots per scanned line in the camera, and the addition in the counter 61 of all the dots of an image enables the surface of the weld spot to be measured for each scanned image. This is why the counter 61 is reset to zero by the beginning of image signal. The output of said counter 61 is connected to two comparators 62a and 62b which receive from memories 62c and 62d respectively maximum and minimum surfaces between which the surface of a weld spot is desired to be located. These counters, when the measured surface is either larger or smaller than the surfaces tolerated, deliver a signal to a flip flop 64 by means of an OR gate 63. Said flip flop then triggers the stopping of the welding apparatus via the OR gate 52 and the terminal 28.

The output of the counter 61 is also connected to a digital-analog converter 65 which furnishes a signal adapted to regulate the welding current of the welding apparatus, via the terminal 26 and the line 27.

The flip flop 64 receives a reset to zero signal from the end of image signal.

The assembly 48, 50, 51 measures the errors of maximum width of the monitored weld point.

A counter 48 of dots validated per line receives the signals from the clock 46 via the AND gate 47, when said latter is validated by the level of the video signal (comparator 40). Said counter 48 also receives as reset to zero signal the beginning of line signal coming from the terminal 25 via lead 35. The output of the counter 48 is connected to a comparator 50 which receives from the memory 50' reference information concerning the desired width for the weld spot and which delivers the signal to a flip flop 51 when the widest line width of the image of the monitored weld spot exceeds the predetermined maximum width. The flip flop 51 then activates the terminal 28 via the OR gate 52. The flip flop 51 receives, at each end of line, a reset to zero signal via lead 35.

The assembly 54,55,56,57,58a,58b,59 enables the errors in symmetry of a weld spot to be determined.

The counter 54 of total dots per line receives the signals from clock 46, and is reset to zero at each beginning of line. It therefore counts the number of dots contained in each line. Its output is connected to a comparator 55 which determines the desired centre of each line due to the information contained in the memory 55'. Said comparator is connected to a counter 56 which receives at its counting input the validated signals issuing from AND gate 47 and is reset to zero at each beginning of line.

The counter 56 counts the validated dots of each line (dots of the image of the weld spot) as far as the theoretical centre of said line, and then counts down the validated dots from said centre. It therefore furnishes at its output the positive or negative difference between the centre of the weld spot and its limits on either side of said centre, at each line scanned in the camera. These differences are compared at 58a or 58b with the tolerated differences stored in memories 58c and 58d. When these differences exceed the tolerances, the comparator 58a or counter 58b, delivers a signal to a flip flop 60 via an OR gate 59. Said flip flop 60 receives the end of line signal as reset to zero signal and activates the terminal 28 via the OR gate 52.

A memory 57, receiving a reset to zero signal constituted by the end of line signal, is interposed between the counter 56 and the comparators 58a and 58b, to allow a longer period of triggering of a possible error in symmetry signal, said memory being, by its very conception, reset to zero with the scanning duration of a delay line.

It is known that, in the welding apparatus of the type concerned by the invention, a defect in one weld spot is not an isolated fact (one defective spot being disposed between satisfactory spots) but, on the contrary, signifies that the adjacent weld spots are also defective and that this comes from a misadjustment of the apparatus. Furthermore, such machines are generally satisfactorily adjusted for a long period, misadjustment occurring only progressively. Consequently it is sometimes unnecessary for the electronic monitoring system according to the invention to function continuously, but on the contrary it may be made to function from time to time to verify the quality of the weld points episodically.

During the periods when the electronic monitoring system is not in operation, it is, however, possible to monitor the quality of the weld spots by presenting in front of the screen 18 of the cathode-ray tube 17 a standard image 61 of a correct weld spot, reproduced on a translucent support and each isothermal zone of which is coloured with the complementary colour of the corresponding coloured zone of the image on the screen 18, said standard image 61 being superposed on the image on the screen.

In this way, if the superposition of image 61 and of the image on the screen 18 is perfect and if the colours are perfectly complementary, an eye 62 observing the screen 18 through the image 61 will see only a uniformly black or brown shading whilst if there is a defect in welding, this defect immediately appears by local formation of a coloured or white shading or band.

Figure 7:
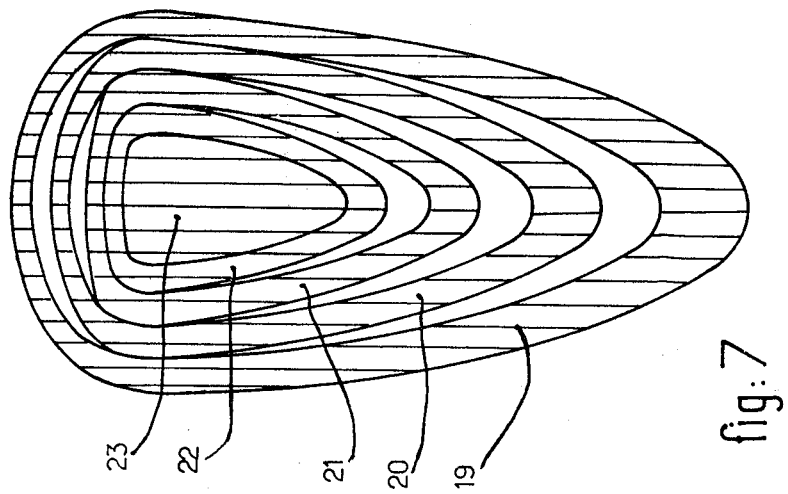

In practice, the isothermal zones 19 to 23 are separated by well defined more or less wide black bands and, in the case of a correct welding, the image shown in FIG. 7 is obtained when the shaded screen according to the invention is placed in front of the screen of said monitor.

Figure 8:
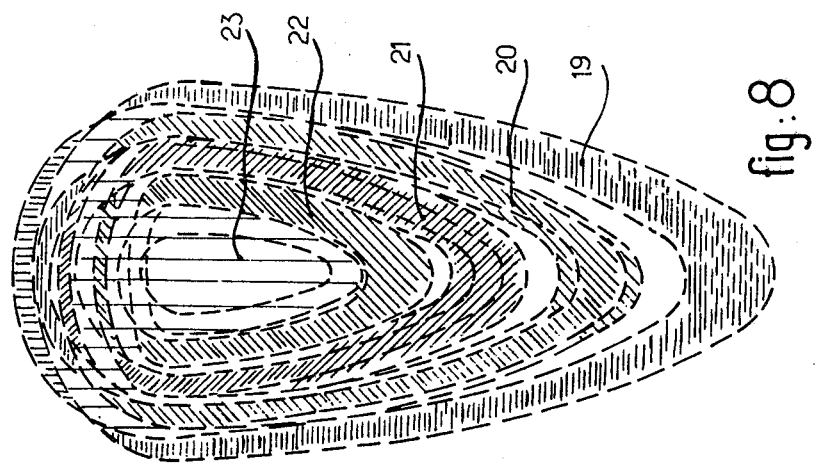
FIGS. 7 and 8 show the infrared image of a weld spot as seen through a complementary filter, in the case of the weld point being correct or incorrect, respectively.

Under the same conditions, if the weld is defective, the image illustrated in FIG. 8 is for example obtained where the zones hatched differently from those of FIG. 7 are white or of various colours.

What we claim is:

1. A method for monitoring weld spots produced by resistance spot welding, comprising the steps of:
    observing a newly formed resistance weld spot at a predetermined time in its cooling with a video camera which scans an image of said weld spot with a plurality of adjacent scanning lines and produces an electrical signal corresponding to the instantaneous level of infrared radiation from said spot;
    determining the existence of a value of said signal during scanning of said spot under observation which exceeds a predetermined reference value, said reference value corresponding to the electrical signal level produced at the periphery of a reference weld spot observed by said camera under the same conditions, and
    comparing the electrical signals above said reference value obtained during scanning of said spot under observation along one dimension thereof with those obtained during scanning of said reference spot as a measure of said dimension with respect to the corresponding dimension of said reference spot.

2. A method in accordance with claim 1 wherein said dimension is the length of said spot and wherein the scanning lines in which the electrical signal exceeds said reference value are counted and compared to the number of corresponding scanning lines of the reference weld spot.

3. A method in accordance with claim 1 wherein said dimension is the width of the weld spot under observation, which method includes the further steps of:
    producing along a scanning line in the image of said weld spot under observation a series of imaginary dots defined by a clock during such time as the video signal exceeds said reference value; and
    counting the number of dots in said scanning line and comparing said number with the number obtained during scanning of said reference weld spot.

4. A method in accordance with claim 3 wherein the total number of said dots in all scanning lines in the image of said weld spot under observation is obtained and compared with the corresponding total number of dots in the image of said reference weld spot as a measure of the area of said weld spot under observation in comparison to the area of said reference weld spot.

5. A method in accordance with claim 4 wherein the difference between the total number of dots counted in the area of the weld spot under observation in comparison with the total number of such dots in the reference weld spot is used to control the amount of welding energy used in producing a succeeding weld spot.

6. A method in accordance with claim 3 wherein the numbers of said dots which fall on either side of a theoretical longitudinal axis of the weld spot under observation are obtained and compared as a measure of the symmetry of said weld spot, the theoretical longitudinal axis of said spot being determined by scanning of the reference weld spot.

7. Resistance welding apparatus including means for monitoring weld spots produced thereby, said apparatus comprising:
an electrically energized welding head;
a video camera sensitive to infrared radiation and operatively attached to said head in position to observe a weld spot produced thereby, said camera scanning an image of said spot with a plurality of adjacent scanning lines and producing an electrical signal which corresponds to the instantaneous level of infrared radiation from said weld spot;
electronic means for determining the existence of a value of said signal during scanning of said spot under observation which exceeds a predetermined reference value, said reference value corresponding to the electrcial signal level produced at the periphery of a reference weld spot observed by said camera under the same conditions;
electronic means for comparing the electrical signals above said reference value obtained during scanning of said spot under observation along one dimension thereof with those obtained during scanning of said reference spot as a measure of said dimension with respect to the corresponding dimension of said reference spot; and
means activated by a difference between said dimension of said weld spot under observation and said corresponding dimension of said reference weld spot for controlling the operating parameters of said welding head.

8. A welding apparatus in accordance with claim 7 including electronic means for comparing the length of said weld spot under observation with that of said reference weld spot by counting the scanning lines in which the electrical signal exceeds said reference value.

9. A welding apparatus in accordance with claim 7 including electronic means for producing along a scanning line in the image of said weld spot under observation a series of imaginary dots defined by a clock during such time as the video signal exceeds said reference value;
electronic means for counting the number of dots in said scanning line and comparing said number with the corresponding number of dots obtained during scanning of said reference weld spot, whereby the width of said weld spot under observation can be compared with the width of said test weld.

10. A welding apparatus in accordance with claim 9 including electronic means for counting the total number of said dots in all scanning lines in the image of said weld spot under observation and for comparing said total number with the corresponding total of dots in the image of said reference weld spot, whereby the area of said weld spot under observation can be compared to the area of said reference weld spot.

11. A welding apparatus in accordance with claim 9 including means for counting and comparing the numbers of said dots which fall on either side of the theoretical longitudinal axis of the weld spot under observation, whereby the symmetry of said weld spot can be determined.

12. A welding apparatus in accordance with claim 7 further including a cathode-ray tube receiving the video signal from said camera and producing an image of a weld spot under observation.

13. A welding apparatus in accordance with claim 12 including a translucent plate on which is reproduced the image of infrared radiation of a reference weld spot, different temperature zones of said image being reproduced on said transparent plate in colors complementary to those with which the infrared image of the weld spot under observation is reproduced on said cathode-ray tube, said translucent plate being arranged such that the image of said weld spot under observation is observed through said translucent plate, whereby a uniformly colored image will be seen if said weld spot under observation corresponds with said reference weld spot.

* * * * *